United States Patent
Rogers et al.

(10) Patent No.: US 9,259,277 B2
(45) Date of Patent: Feb. 16, 2016

(54) INSTRUMENT ACTUATION INTERFACE

(75) Inventors: Theodore W. Rogers, Alameda, CA (US); John Ryan Steger, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 301 days.

(21) Appl. No.: 13/360,421

(22) Filed: Jan. 27, 2012

(65) Prior Publication Data

US 2012/0289974 A1    Nov. 15, 2012

Related U.S. Application Data

(60) Provisional application No. 61/485,697, filed on May 13, 2011.

(51) Int. Cl.
*A61B 19/00* (2006.01)
*A61B 17/00* (2006.01)

(52) U.S. Cl.
CPC ... *A61B 19/2203* (2013.01); *A61B 2017/00477* (2013.01); *A61B 2019/2242* (2013.01)

(58) Field of Classification Search
CPC ............ A61B 2017/00477; A61B 2019/2242; A61B 1/00112; A61B 19/08; A61B 19/081; A61B 2017/3419; A61B 19/38; A61B 2019/4868; A61B 19/2203; B25J 9/1045
See application file for complete search history.

(56) References Cited

U.S. PATENT DOCUMENTS

| | | | |
|---|---|---|---|
| 7,727,244 B2 | 6/2010 | Orban, III | |
| 2006/0052664 A1 | 3/2006 | Julian | |
| 2007/0156019 A1 | 7/2007 | Larkin | |
| 2009/0324161 A1 | 12/2009 | Prisco | |
| 2010/0082041 A1 | 4/2010 | Prisco | |
| 2010/0094088 A1 | 4/2010 | Ohline | |
| 2010/0174244 A1* | 7/2010 | Dankelman et al. | 604/264 |
| 2010/0175701 A1* | 7/2010 | Reis et al. | 128/852 |
| 2010/0268250 A1* | 10/2010 | Stuart et al. | 606/130 |
| 2011/0282359 A1* | 11/2011 | Duval | 606/130 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

*Primary Examiner* — Gary Jackson
*Assistant Examiner* — Scott T Luan (57) ABSTRACT

A system includes a medical instrument that includes a termination fixture, an actuated element, and drive members coupled to the actuated element and extending to the termination fixture. The termination fixture provides an interface that exposes portions of the drive member to direct movement by an external system that may include a manipulator and a sterile barrier.

23 Claims, 6 Drawing Sheets

INSTRUMENT ACTUATION INTERFACE

BACKGROUND

Figure 1A:
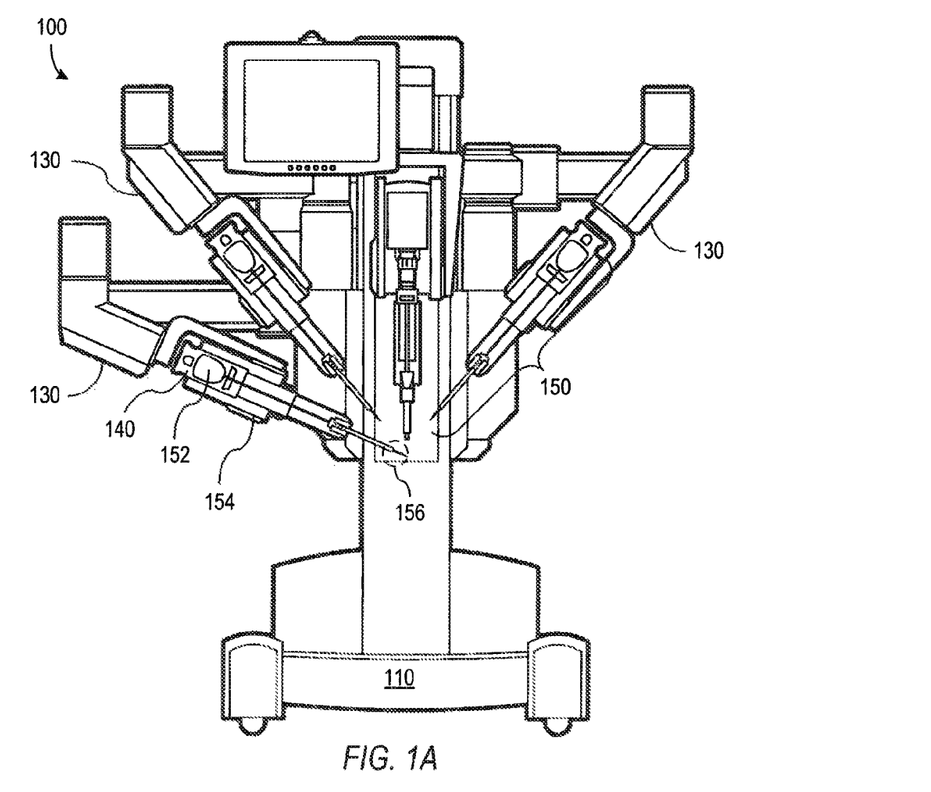
FIG. 1A shows a medical system that can employ removable instruments with mechanical interfaces in accordance with an embodiment of the invention.

Robotically controlled medical systems such as employed for minimally invasive medical procedures can include complex equipment to precisely control and drive medical instruments. (As used herein, the terms "robot" or "robotically" and the like include teleoperation or telerobotic aspects.) FIG. 1A illustrates an example of a known robotically controlled system 100. System 100, which may, for example, be part of a da Vinci® Surgical System available from Intuitive Surgical, Inc., includes a patient-side manipulator 110 having multiple arms 130. Each arm 130 has a docking port 140 that generally includes a drive system with a mechanical interface for mounting and providing mechanical power for operation of an instrument 150. Arms 130 can be used during a medical procedure to move and position respective medical instruments 150 for the procedure.

Figure 1B:
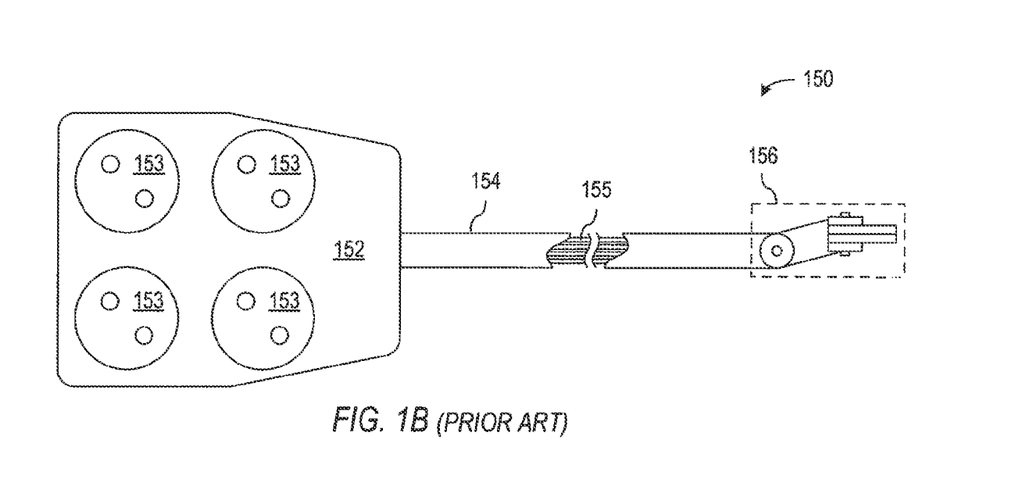
FIG. 1B shows a bottom view of a medical instrument having a backend mechanism that provides a known mechanical interface for actuation of the instrument.

FIG. 1B shows a bottom view of a known medical instrument 150. Instrument 150 generally includes a transmission or backend mechanism 152, a main shaft 154 extending from the backend mechanism 152, and a functional tip 156 at the distal end of main shaft 154. Tip 156 generally includes a medical tool such as a scalpel, scissors, forceps, or a cauterizing instrument that can be used during a medical procedure. Drive members 155 such as cables or push-pull rods connect to tip 156 and extend through main shaft 154 to backend mechanism 152. Backend mechanism 152 typically provides a mechanical coupling between drive members 155 of instrument 150 and motorized axes of the mechanical interface of docking port 140. In particular, backend mechanism 152 typically contains mechanical elements such as capstans, gears, and levers that convert rotational movement of drive motors into linear motion of tendons or push rods 155.

Instruments 150 of system 100 can be interchanged by removing one instrument 150 from a docking port 140 and then installing another instrument 150 in place of the instrument removed. Equipment such as patient-side manipulator 110 is often covered for a medical procedure by a sterile barrier because of the difficulty in cleaning and sterilizing complex equipment between medical procedures. These sterile barriers can include a plastic sheet and a sterile adaptor (not shown) that is interposed between docking port 140 and instrument backend 152. However, instruments 150 are on the patient side of the sterile barrier and are generally subject to surgical sterile protocols. The complexity of backend mechanism 152 can make sterilization of instruments 150 difficult particularly if an instrument is intended to be reused for multiple medical procedures. The complexity of backend mechanism 152 also increases the cost of instrument 150, which is particularly a concern when an instrument is intended to be a single use device.

SUMMARY

In accordance with an aspect of the invention, a minimally invasive medical system minimizes the complexity of the mechanical interface portion on the instrument. In particular, a manipulator that is outside a sterile barrier can use a mechanical interface with nearly direct access to connecting members such as cables or push-pull rods on the patient side of the sterile barrier. For example, in some embodiments, only portions of the sterile barrier are between the manipulator and the tendon or push-pull rod that the manipulator actuates.

One specific embodiment of the invention is a system including a medical instrument having a main shaft, an actuated element connected to the main shaft, a drive member connected to the actuated element and extending through the main shaft; and a termination fixture at a proximal end of the main shaft. The drive member terminates at the termination fixture, where the termination fixture provides an interface that exposes a portion of the drive member to direct access and movement by a system external to the medical instrument. In particular, the external system can include a manipulator system and a sterile barrier.

Another embodiment of the invention is a method for operating a medical instrument. The method includes installing a sterile barrier that is in direct contact with a drive member of the medical instrument. The drive member may be a tendon, rod, or similar structure that extends through a main shaft of the instrument and connects to an actuated element of the instrument. After the sterile barrier is installed, a manipulator operates or acts on the sterile barrier to transfer force through the sterile barrier to the drive member to thereby actuate the actuated element of the instrument.

Yet another embodiment of the invention is a method for constructing and using a medical instrument. In particular, a medical instrument having one or more tendons that extend from a proximal end of the instrument to an actuated element at a distal end of the instrument can be constructed without tension in the tendons or with tensions below those required for normal operation of the instrument when in use attached to a manipulator. The construction process may thus be simplified, particularly because some manufacturing processes are made more difficult by pre-tensioning of tendons. The instrument without tension in the tendons can be used by first engaging the medical instrument with a manipulator to create tension in the tendons and then operating the manipulator to pull the tendons and actuate the medical instrument.

BRIEF DESCRIPTION OF THE DRAWINGS

Use of the same reference symbols in different figures indicates similar or identical items.

DETAILED DESCRIPTION

In accordance with an aspect of the invention, a backend mechanism of a medical instrument can be simplified to reduce the amount of hardware required in the medical instrument. In particular, the capital equipment such as a patient-side manipulator (PSM) or other instrument manipulator can be adapted to act on extended drive members of the instrument directly through a sterile barrier. The extended drive members, which may be tendons or push-pull rods, can be brought to a simple termination fixture at the proximal end of the main shaft of the instrument. The fixture and/or main shaft can then be plugged directly into a sterile barrier and a port of a robotic control system. Mechanical elements such as capstans, input dogs, levers, or other mechanisms conventionally included in a backend of a medical instrument are not part of the instrument and are not subject to surgical sterilization protocols.

Figure 2A:
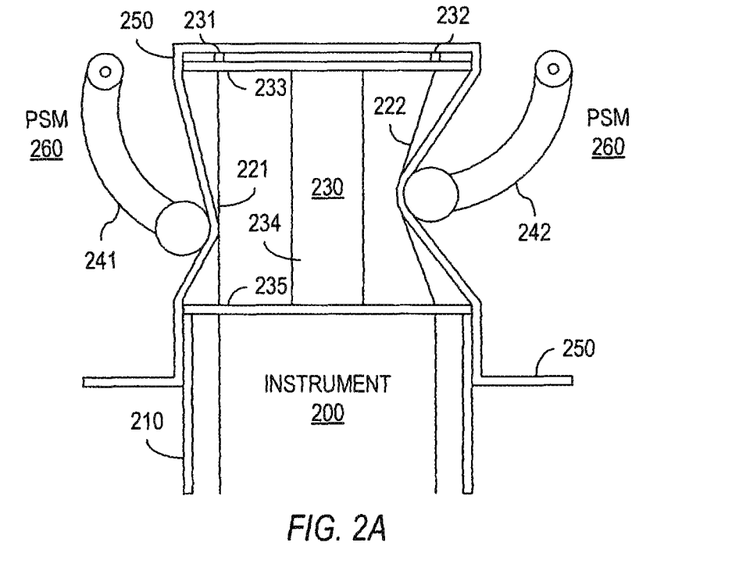
FIGS. 2A and 2B illustrate operation of a portion of a medical system in which a mechanical interface of an instrument makes suspended portions of tendons accessible to manipulators.

FIG. 2A shows a proximal end of an instrument 200 having a main shaft 210 through which tendons 221 and 222 extend. Main shaft 210 may be a rigid tube, a flexible tube, or a set of linked vertebrae. Each tendon 221 or 222 can be any type of flexible connecting member such as a cable, a filament, a tube, or a rod that is able to support tension created by pulling on the connecting member but is not required to support compression resulting from pushing on the connecting member. The proximal ends of tendons 221 and 222 terminate at a fixture 230 that is attached to the proximal end of main shaft 210, and distal ends (not shown) of tendons 221 and 222 attach to one or more actuated mechanical members or distal elements (not shown) of instrument 200. Such actuated distal elements of robotically medical instruments are well known in the art and may be, for example, part of an end effector such as tip 156 of FIG. 1B or may be an actuated vertebra that is part of main shaft 210. For illustration of the operation of an exemplary embodiment of instrument 200, tendons 221 and 222 are presumed to connect to the same distal element of instrument 200 so that pulling on tendon 221 causes the mechanical member to move or rotate in a first direction and pulling on tendon 222 causes the mechanical member to move or rotate in an opposite direction. In one commonly employed configuration of an articulated element, pulling in a length of one tendon 221 or 222 requires feeding out of an equal length of the other tendon 222 or 221, and tendons 221 and 222 may be opposite ends of a single cable that wraps around a portion of the element. Many other configurations for articulation of medical instruments are known and could be employed in different embodiments of instrument 200.

Tendons 221 and 222 exit the proximal end of main shaft 210 and pass through holes or grooves in a plate 235 and a plate 233 of termination fixture 230. Crimps, bends, beads, rings, or similar structures 231 and 232 in or on tendons 221 and 222 can be used to limit movement of the proximal ends of tendons 221 and 222 in the distal direction and may be attached or affixed to plate 233 or may be free to be pulled in the proximal direction from plate 233. Plate 233 attaches to plate 235 and the end of main shaft 210 through a support 234. Support 234 may be rigid or may provide spring tension to plate 233 and attached tendons 221 and 222 for a limited range of motion that is taken up when instrument 200 engages an instrument manipulator 260. Support 234 provides a separation between plates 233 and 235, so that portions of each tendon 221 or 222 are suspended and accessible between plates 233 and 235. The remaining portions of tendons 221 and 222 extend distally from plate 235 through main shaft 210 to an actuated distal element of instrument 200.

Manipulators 241 and 242, which are part of PSM 260 outside a sterile barrier 250, can act on the suspended portions of respective tendons 221 and 222 that are exposed by fixture 230. In particular, a sideways displacement of a portion of a tendon 221 or 222 between plates 233 and 235 applies tension and causes displacement of the distal end of the displaced tendon 221 or 222, since plate 233 and structures 231 and 232 prevent the proximal ends of tendons 221 and 222 from moving in the distal direction. Instrument 200 during a medical procedure will be within an area subject to surgical sterile protocols, while manipulators 241 and 242 and the rest of the PSM will be outside sterile barrier 250. Instrument 200 has the advantage that sterile barrier 250 may be as simple as a plastic bag interposed between tendons 221 and 222 and manipulators 241 and 242.

Figure 2B:
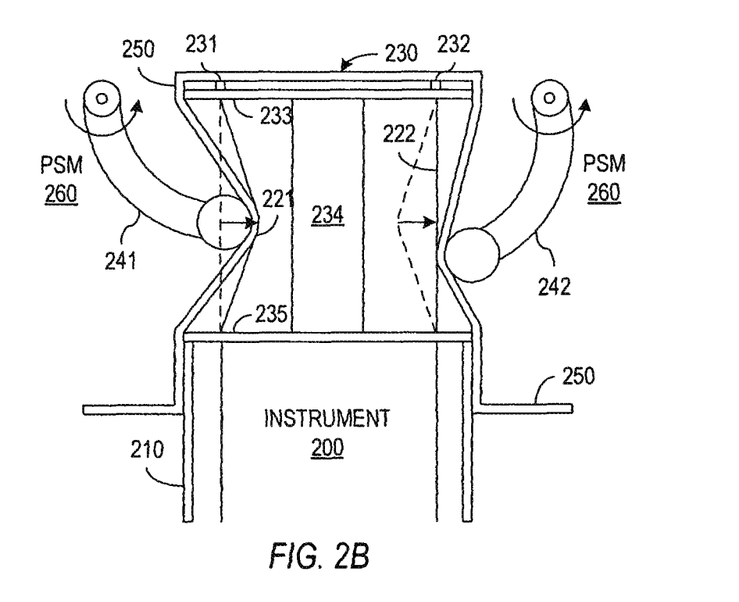

FIG. 2A shows a configuration of instrument 200 in which tendon 221 is straight and manipulator 242 has pushed a portion of tendon 222 toward the center axis of termination fixture 230. FIG. 2B illustrates movement of manipulator 241 that pushes a suspended section of tendon 221 toward the center axis of termination fixture 230 and movement of manipulator 242 that releases the deflection of tendon 222. Increasing the deflection of tendon 221 pulls in the distal end of tendon 221, and releasing the deflection of tendon 222 feeds a portion of tendon 222 out of the termination fixture 230 toward the distal end of instrument 200. Accordingly, movement of manipulators 221 and 222 can be used to actuate a distal element coupled to tendons 221 and 222.

FIGS. 2A and 2B shows an arrangement in which manipulators 241 and 242 of PSM 260 can push on the sides of tendons 221 and 222 through intervening sterile barrier 250 and deflect portions of tendons 221 and 222 toward a center axis of main shaft 210. Alternatively, manipulators 241 and 242 could be designed to pull or pluck respective tendons 221 and 222 to cause deflections in any direction perpendicular to the lengths of tendons 221 and 222.

Figure 3A:
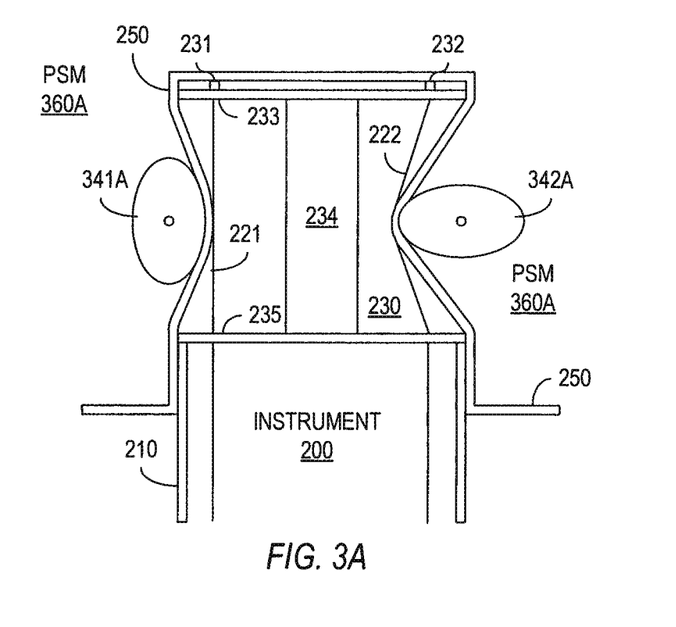
FIGS. 3A and 3B show portions of medical systems in accordance with embodiments of the invention respectively using cams and rack-and-pinion manipulators for the tendons in a medical instrument.
Figure 3B:
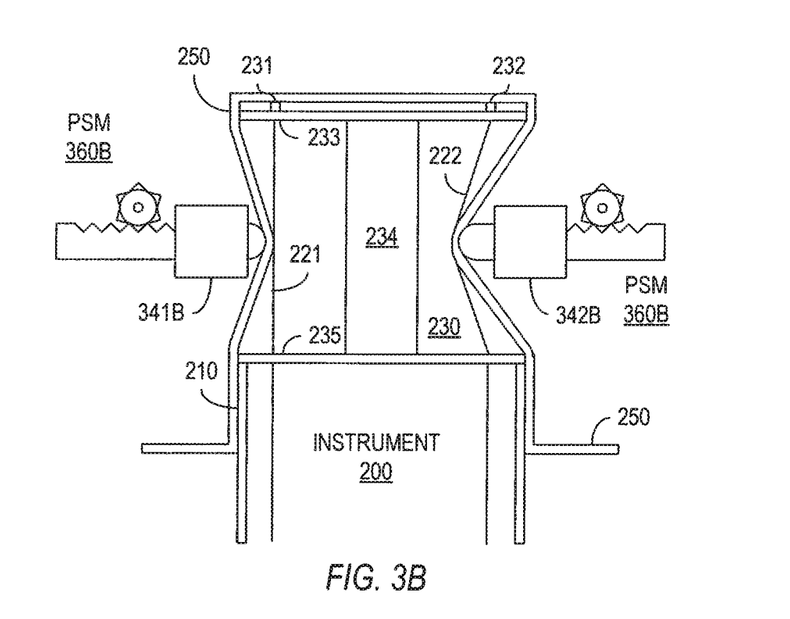

Manipulators 241 and 242 for tendons 221 and 222 may be implemented using fingers, cams, or rollers, which contact respective tendons 221 and 222. FIGS. 2A and 2B show an embodiment in which manipulators 241 and 242 are fingers that contact tendons 221 and 222 and rotate about an offset axis to push on tendons 221 and 222. Other methods for moving tendons are possible. FIG. 3A, for example, shows a portion of a medical system in which manipulators 341A and 342A are cams that contact tendons 221 and 222 and are shaped so that rotations of the cams deflect tendons 221 and 222. FIG. 3B shows a portion of a medical system in which manipulators 341B and 342B are implemented using rack and pinion system in which rack portions contact tendons 221 and 222 through sterile barrier 250 and a pinion gear is coupled to a drive motor (not shown) so that rotation of the pinion gear moves the rack and deflect tendons 221 and 222. The manipulators, whether employing fingers, cams, or other structures to contact the tendons, may be actuated independently or may be geared or coupled together within PSM 260, 360A, or 360B to accomplish coordinated motion of two or more tendons if necessary to achieve smooth articulation of instrument 200. The gearing or coupling for articulation of instrument 200 may be independent of a mechanism used to engage or disengage the manipulators and tendons during installation or removal of instrument 200.

A process for installing instrument 200 in PSM 260 of FIG. 2A or 2B or PSM 360A or 360B of FIG. 3A or 3B needs to engage manipulators 241 and 242, 341A and 341B, or 341B and 342 and respective tendons 221 and 222 so that the PSM can control actuation of instrument 200. (The following describes a process for installing instrument 200 in PSM 260 of FIG. 2A or 2B. Similar processes may be used for installation in PSM in accordance with other embodiments of the invention.)

Inserting the proximal end (e.g., termination fixture 230) of instrument 200 into a matching port of PSM 260, e.g., port 140 of system 100 as shown in FIG. 1A, will generally bring tendons 221 and 222 into the range of motion of respective manipulators 241 and 242 but may not bring tendons 221 and 222 into contact with manipulators 241 and 242. Accordingly, PSM 260 will generally need to move manipulators 241 and 242 into contact with tendons 221 and 222. In one embodiment, tendons 221 and 222 in instrument 200 may initially have slack that is redistributed or removed as manipulators 241 and 242 move to fully engage respective tendons 221 and 222. Alternatively, plate 233 or 235 or tendons 221 and 222 may be spring loaded to provide pre-tension in tendons 221 and 222 that may be less than the tension require for normal use of instrument 200, and initially engaging instrument 200 with manipulators 241 and 242 can involve pushing the spring or springs to a limit of its or their range of motion or locking the pre-tension system so that the proximal ends of tendons 221 and 222 remain immobile during operation of instrument 200. However, instrument 200 without pre-tensioned tendons 221 and 222 may be easier to construct and less susceptible to thermal effects during high temperature sterilization than would a pre-tensioned instrument. A lack of tendon tension or reduced tendon tension in tendons 221 and 222 when instrument 200 is not engaged with manipulator 260 may provide for greater instrument durability when instrument 200 undergoes cleaning and sterilization processes. In particular, a sterilization process in an autoclave or similar high temperature system differentially elongates tendons 221 and 222 relative to main shaft 210 and other structures because of differences in the coefficients of thermal expansion of the materials that may be used in different parts of instrument 200, and the differential expansion can stretch or damage tendons 221 and 222. Reduced tension in tendons 221 and 222 during reprocessing can reduce or eliminate damage that might otherwise occur in high temperature sterilization processes. Also, a lack of tendon tension or reduced tendon tension in instrument 200 when instrument 200 is not engaged with 260 manipulator may provide easier removal of instrument 200 when disengaging instrument 200 from manipulator 260 during surgery.

Manipulators 241 and 242, during the installation process for instrument 200, can simultaneously apply the same small initial force to remove slack from tendons 221 and 222 without actuating instrument 200. The deflections of tendons 221 and 222 when manipulators 241 and 242 apply constant initial force will generally depend on how instrument 200 is posed, i.e., on the initial position of the distal element articulated by tendons 221 and 222 and on the shape of main shaft 210 when main shaft 210 is jointed or flexible. Thus, if there is no creep or stretch in tendons 221 and 222, the pose of instrument 200 may be inferred from the sideways displacements that the initial force during the installation process produces in tendons 221 and 222 and any other actuating tendons (not shown) of instrument 200. This installation process can automatically compensate for cable creep or stretch over the life of the instrument, but if tendons 221 and 222 have stretched by an unknown amount, an instrument control system for the PSM may establish the initial position of instrument 200 using other techniques. For example, distal position sensing using a shape sensor or keeping the distal portion of instrument 200 fixed in a rigid tube during engagement could be used to establish the initial pose or instrument 200. Some examples of shape sensors are described in U.S. Pat. App. Pub. No. US 2007/0156019 A1 (tiled Jul. 20, 2006), entitled "Robotic Surgery System Including Position Sensors Using Fiber Bragg Gratings" by Larkin et al., and U.S. patent application Ser. No. 12/164,829 (filed Jun. 30, 2008) entitled "Fiber optic shape sensor" by Giuseppe M. Prisco, both of which are incorporated herein by reference. Once manipulators 241 and 242 engage tendons 221 and 222 further movements of manipulators 241 and 242 can be used to articulate instrument 200.

Figure 4:
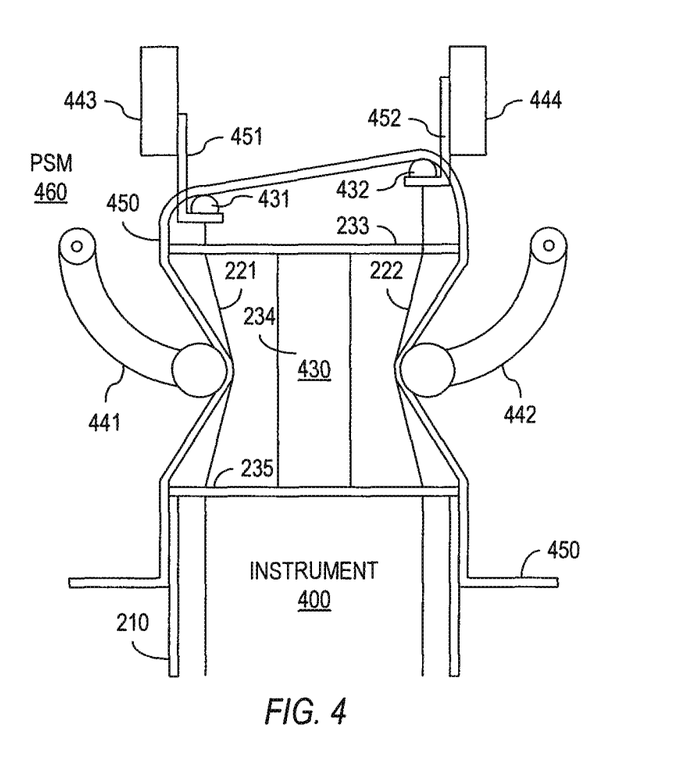
FIG. 4 shows a portion of a medical system in accordance with an embodiment of the invention with manipulators that act on the sides of suspended portions of tendons and on proximal ends of the tendons.

Separate systems can be employed for tensioning an instrument during installation and actuation of the instrument during operation. FIG. 4, for example, shows an instrument 400 that is used with a PSM 460 that has two sets of manipulators. Manipulators 441 and 442 operate on suspended portions of tendons 221 and 222, and manipulators 443 and 444 operate on the proximal ends of tendons 221 and 222. The two sets of manipulators can be used for different purposes. For example, manipulators 441 and 442 may be used to engage or disengage tendons 221 and 222 during installation or removal of instrument 400 at PSM 460, and manipulators 443 and 444 may be used to pull on tendons 221 and 222 for actuation of instrument 400. Instrument 400 is similar to instrument 200 of FIGS. 2A, 2B, 3A, and 3B and includes a main shaft 210 and tendons 221 and 222 that may be as described above. Instrument 400 also includes a termination fixture 430 that includes plates 233 and 235 connected by a support 234 as described for fixture 230 above, but in fixture 430, tendons 221 and 222 are not affixed to plate 233. The proximal ends of tendons 221 and 222 in instrument 400 pass through holes in plate 233 and terminate in end caps, beads, rings, crimps, or other structures 431 and 432 that are shaped to be gripped and pulled. For example, end structures 431 and 432 may be shaped to fit into respective forked adapters 451 and 452, which may be fixtures of a sterile barrier 450, and manipulators 443 and 444 can be adapted to grip and pull on forks 451 and 452. In one embodiment, adapters 451 and 452 are solid structures that are fixed in a plastic sheet that is part of sterile barrier 450, and slack or flexibility in sterile adapter 450 permits manipulators 443 and 444 to move adapters 451 and 452 (and end structures 431 and 432 coupled to adapters 451 and 452) through a range of motion required for use of instrument 400.

During an exemplary process for installation of instrument 400, manipulators 443 and 444 grasp the respective end structures 431 and 432 of tendons 221 and 222, e.g., through forked adapters 451 and 452 of sterile barrier 450, then manipulators 441 and 442 advance to remove slack from respective tendons 221 and 222. Instrument 400 can then be actuated by the axial motion of end manipulators 443 and 444, while side manipulators 441 and 442 remain in their initial engaged positions. Alternatively, manipulators 443 and 444 can be used to remove slack, and manipulators 441 and 442 can deflect tendons 221 and 222 for operation of instrument 400 as described above. To facilitate axial movement of tendons 221 and 222 during actuation of instrument 400, sterile barrier 450 may include a resilient, low friction surface that contacts the sides of tendons 221 and 222. Again, a non-pre-tensioned instrument in an arbitrary pose may be engaged and actuated, if sufficient information on the distal position of instrument 400 is separately available when stretching or creep in tendons 221 and 222 are potential issues.

Instrument 400 can also be used with a PSM lacking side manipulators 441 and 442. In that embodiment of the invention, the installation process for instrument 400 includes end manipulators 443 and 111 moving to their most distal position, moving radially or sideways to engage end structures 431 and 432, and then withdrawing proximally with low force to remove the slack from each tendon 221 and 222. Since sideways deflections of tendons 221 and 222 are not used, tendons 221 and 222 can be replaced by push-pull rods or other rigid connecting members. Push-pull rods can employ rods, tubes, or other structures that are sufficiently rigid to support compression resulting from manipulators 443 and 444 pushing on the ends of the push-pull rods. When manipulators 443 and 444 engage push-pull rods, control processes that pull or push on the push-pull rods may be employed for actuation of instrument 400. It may be noted that instruments employing push-pull rods can actuate a movable member through a single push-pull rod, so that complementary movement of pairs of drive members are not required.

Figure 5:
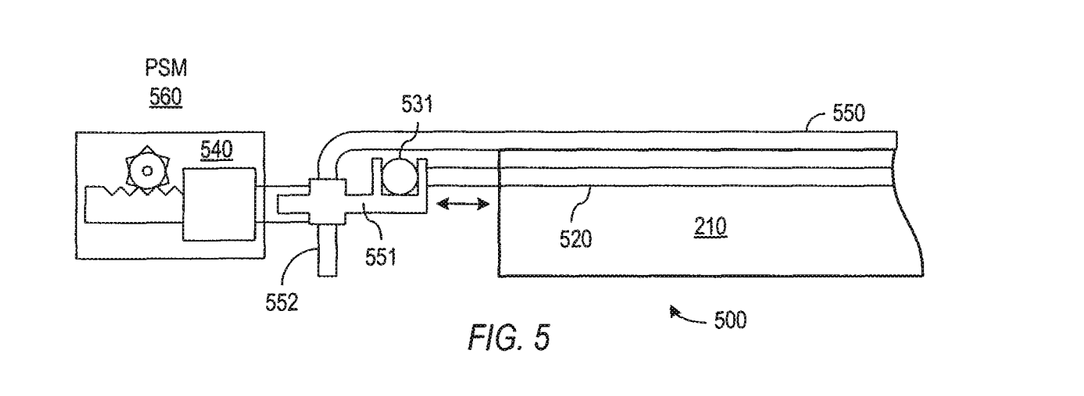
FIG. 5 shows a side view of a medical system including an instrument having a push-pull rod.

FIG. 5 shows a portion of an instrument 500 employing a push-pull rod 520 that extends through a main shaft 210 from actuated element (not shown) at the distal end of push-pull rod 520 to an engagement structure 531 at the proximal end of push-pull rod 520. As described above, push-pull rod 520 can be a rod, a tube, or any extended structure capable of withstanding the tension and compression need for operation instrument 500. A sterile barrier 550 separates medical instrument 500 from a manipulator system 560. In the illustrated embodiment, sterile barrier 500 includes an adapter 551 that may be fused into a portion of a barrier sheet 552. A manipulator 540, e.g., a rack-and-pinion system 540 connects to adaptor 551, which in turn connects to structure 530 on push-pull rod 520. Manipulator 540 can move push-pull rod 520 by pushing or pulling on adaptor 551. In one embodiment of the invention, adaptor 551 is solid structure fused into sheet 552 and relies on flexibility or slack in sheet 552 to accommodate the required range of motion of push-pull rod 520. Alternatively, adaptor 531 can be a multi-component structure including a slide that moves with push-pull rod 520 and a guide that remains fixed in sheet 552. In yet another alternative embodiment, adaptor 551 may connect via a mechanical coupling to manipulator 540 without breeching sterile barrier 550, thus simplifying the construction of sterile barrier sheet 552 by not requiring a fused component. This type of coupling between manipulator 540 and adaptor 551 may rely on the flexibility and slack in sheet 552 to conform to the interface between the 540 and 551 and to accommodate the required range of motion of push-pull rod 520.

Figure 6:
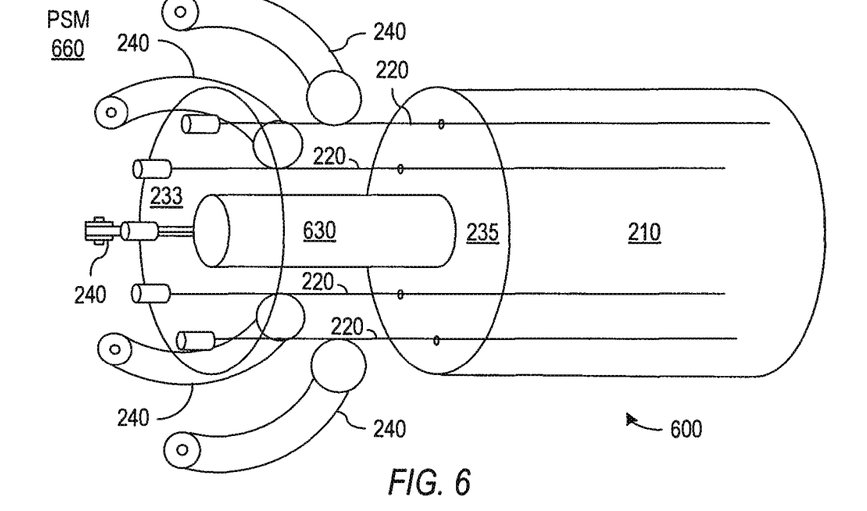
FIG. 6 shows a portion of a medical system in accordance with an embodiment of the invention including a medical instrument having accessible tendons in a cylindrical arrangement.

Robotically controlled medical instruments generally require the use of many drive members for actuation of the medical instrument. Embodiments of the invention can provide manipulator access to those drive members using a termination fixture with different geometry. FIG. 6, for example, illustrates a portion of a medical system including an instrument 600 having a termination fixture 630 that arranges tendons 220 in a cylindrical formation for side access by manipulators 240, which can be implemented using a variety of mechanical systems including but not limited to those described above with reference to FIGS. 2A, 2B, 3A, and 3B. For ease of illustration, a sterile barrier, which would be interposed between a PSM 660 including manipulators 240 and instrument 600, is not shown in FIG. 6.

Figure 7A:
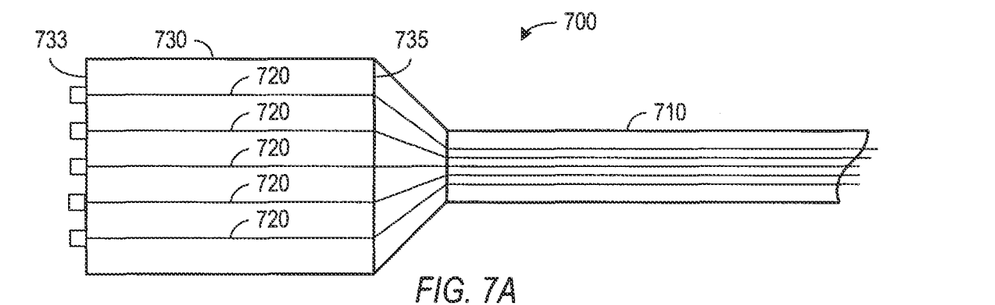
FIG. 7A shows a top view of a medical instrument having accessible tendons in a linear arrangement.
Figure 7B:
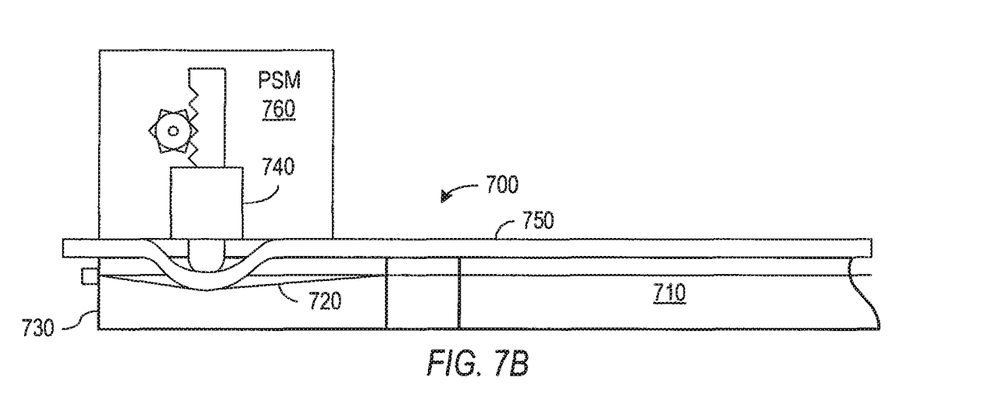
FIG. 7B shows a side view of the medical instrument of FIG. 7A and illustrates a manipulator operating on a tendon through an intervening sterile barrier.

FIG. 7A shows a top view of a portion of a medical instrument 700 in accordance with an embodiment of the invention employing a linear arrangement of tendons 720. In instrument 700, tendons 720 are suspended between walls 733 and 735 of a termination fixture 730 at the proximal end of a main shaft 710 of instrument 700. In particular, tendons 720 have proximal ends that are prevented from moving in a distal direction at wall 733. Tendons 720 extend through and rest on holes or grooves in wall 735 and extend through main shaft 710 to actuate features (not shown) of instrument 700. Fixture 730 can be used to expand the separation between tendons 720 (relative to the spacing within main shaft 710) if more space between tendons 720 is desired in order to improve manipulator access to tendons 720. In particular, the top of fixture 730 can be open so that manipulators 740 in PSM 760 can access tendons 720 as shown in FIG. 7B. FIG. 7B shows a sterile barrier 750 that may be a plastic sheet interposed between manipulators 740 and tendons 720. Manipulators 740 in FIG. 7B employ a rack and pinion structure allowing PSM 760 to control the amount of deflection of a tendon 720 or sideways force applied to the tendon 720 by controlling the movement or torque applied by a drive motor (not shown) for the rack-and-pinion manipulator 740. Many other types of manipulators could be used to achieve the same movement of tendons 720.

Figure 8:
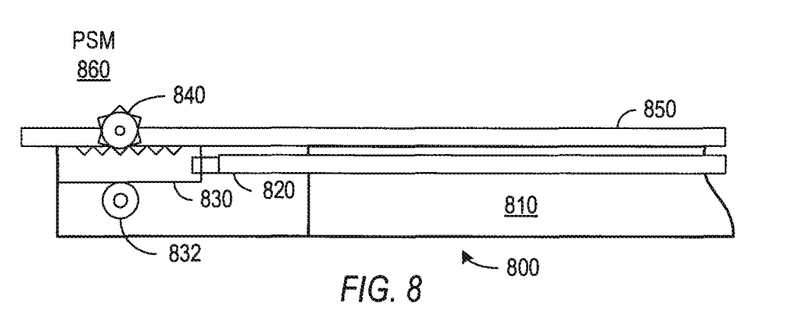
FIG. 8 illustrates a portion of a medical instrument in accordance with an embodiment of the invention using rack and pinion drive at the proximal ends of connecting members.

FIG. 8 shows a portion of an instrument 800 having a mechanical interface exposing a drive member 820 (e.g., a tendon or push-pull rod) for actuation through a pinion gear 840 that may be part of a manipulator system 860 or part of a sterile barrier 850. FIG. 8 shows a single drive member 820 but instrument 800 would typically contain multiple drive members for actuation of instrument 800, and drive members 820 may be arranged cylindrically as illustrated in FIG. 6, linearly as illustrated in FIG. 7A, or in any manner that presents portions of drive members 820 for manipulation by a manipulator system 860 outside of the sterile barrier 850 containing instrument 800. In instrument 800, each drive member 820 exits from the back of the main shaft 810 as a rigid strut terminating in a gear rack 830 that may be part of instrument 800 or alternatively part of an adapter in sterile barrier 850. Gear racks 830 can have a fixed rotational orientation, or each gear rack 830 may have teeth of a constant profile revolved about the axis of the strut. Gear racks 830 are each engaged by respective pinion gears 840 which may be at least part of an adaptor in sterile barrier 850 or part of a manipulator on the PSM side of sterile barrier 850. Idler rollers or gears 832 may be positioned to maintain the correct clearance between racks 830 and driving pinion gears 840. These idlers 732 or the axial position of each rack 830 may further be spring loaded to minimize backlash between gear 840 and rack 830. Given features to align the major axis and the rotational position of instrument 800 with PSM 860 during instrument installation, each rack 830 may be shaped to automatically engage its appropriate driving gear 840 as instrument 800 is inserted axially (in a direction from distal to proximal) into PSM 860. If racks 830 are allowed to back-drive pinion gears 840, PSM 860 may sense the initial position of each rack 830 by observing when pinion gears 840 begins (or stops) turning, and thus determine final position when instrument 800 is seated in a port of PSM 860. Further, if instrument 800 and PSM 860 are constructed such that racks 830 are not back-driven by the insertion process, the distal instrument pose of instrument 800 may be inferred from the initial positions of racks 830. If the installation process includes PSM 860 driving pinion gears 840 to apply and maintain a minimum preload on each rack 830, instrument 800 may be retained in PSM 860 solely by this pre-tension and may later be released for disengagement by releasing this pre-tension.

Figure 9:
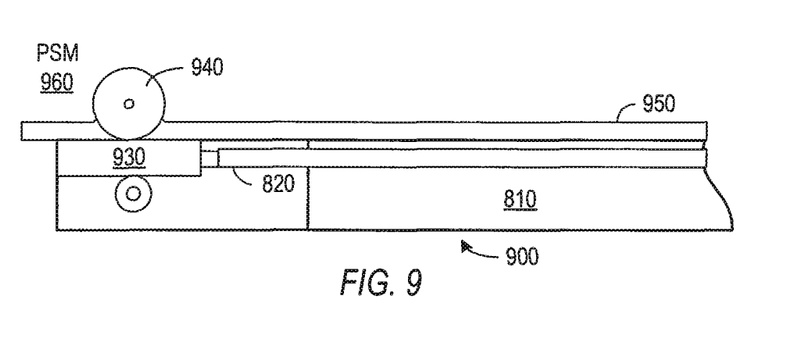
FIG. 9 illustrates a portion of a medical instrument in accordance with an embodiment of the invention using friction drive at the proximal ends of connecting members.

FIG. 9 shows an instrument 900 that may be operated in a manner similar to that of instrument 800 of FIG. 8, but instrument 900 uses a friction drive rather than a rack and pinion drive to move tendons or push-pull rods 820. The back end of each drive member 820 in instrument 900 may simply include a section 930 having a surface on which a drive roller 940 can ride. Section 930 may simply be the end portion of a rod or rigid tubing, flattened or otherwise, that is accessible to a drive roller 940 that is part of a sterile barrier 950 or part of PSM 960. The drive rollers 940 may be composed of high-friction materials, such as rubber, which may wear quickly. Accordingly, it may be advantageous to incorporate drive rollers 940 into a disposable sterile interface component that is part of sterile barrier 950 and is renewed or replaced for each use of instrument 900. Unlike a rack and pinion drive, a friction drive may be allowed to slip under certain circumstances, which may be advantageous to the control scheme of the instrument. See, for example, U.S. patent application Ser. No. 12/286,644, entitled "Passive Preload and Capstan Drive for Surgical Instruments," which describes another type of system that allows tendons to slip relative to the movement of a drive system.

Although the invention has been described with reference to particular embodiments, the description is only an example of the invention's application and should not be taken as a limitation. Various adaptations and combinations of features of the embodiments disclosed are within the scope of the invention as defined by the following claims.

What is claimed is:

1. A system comprising a medical instrument that includes:
   a main shaft;
   an actuated element connected to a distal end of the main shaft;
   a tendon connected to the actuated element and physically extending through the main shaft; and
   an interface at a proximal end of the main shaft and configured to expose a suspended portion of the tendon to direct access and sideways deflection that is located away from ends of the tendon and actuates the actuated element.

2. The system of claim 1, wherein the actuated element comprises a joint operated by the sideways deflection of the tendon.

3. The system of claim 1, wherein the interface comprises a first plate positioned to limit movement of a proximal end of the tendon in a distal direction.

4. The system of claim 3, wherein the interface further comprises a second plate through which the tendon passes, wherein the second plate is positioned so that the suspended portion of the tendon is suspended between the first plate and the second plate.

5. The system of claim 1, wherein the interface further exposes a proximal end of the tendon to longitudinal movement that actuates the actuated element.

6. The system of claim 1, wherein the instrument further comprises a plurality of tendons extending through the main shaft and the interface, wherein for each of the tendons, the interface exposes a suspended portion of the tendon to direct access and movement that actuates the actuated element.

7. The system of claim 6, wherein the exposed suspended portions of the tendons in the interface are arranged cylindrically about an axis of the main shaft.

8. The system of claim 6, wherein the exposed suspended portions of the tendons are arranged in a plane.

9. The system of claim 1, further comprising:
   a patient-side manipulator that physically acts on the drive member to cause actuation of the actuated element; and
   a sterile barrier that is between the patient-side manipulator and the instrument.

10. The system of claim 9, wherein the sterile barrier comprises a sheet that is between the exposed portion of the tendon and the patient-side manipulator, wherein the patient-side manipulator moves the tendon by pressing on the tendon through the sheet.

11. The system of claim 9, wherein the manipulator presses on the tendon through the sheet without other intervening structure.

12. A system comprising a medical instrument that includes:
    a main shaft;
    an actuated element connected to a distal end of the main shaft;
    a drive member connected to the actuated element and physically extending through the main shaft;
    an engagement structure that is on a proximal end of the drive member and is a solid structure shaped to engage a system external to the medical instrument; and
    an interface at a proximal end of the main shaft and configured to expose the engagement structure to direct engagement by an adapter in a sterile barrier and to permit the adapter to move the engagement structure in a direction along a length of the drive member to thereby actuate the actuated element.

13. The system of claim 12, wherein the engagement structure is shaped to engage a fork that is part of the adapter.

14. The system of claim 12, wherein the engagement structure comprises a gear rack positioned in the interface to be engaged by a pinion gear external to the instrument.

15. The system of claim 14, further comprising the sterile barrier, wherein the adapter in the sterile barrier includes a pinion gear that engages the gear rack of the engagement structure.

16. The system of claim 12, wherein the engagement structure comprises a surface positioned and shaped to engage a friction drive external to the instrument.

17. The system of claim 16, further comprising the sterile barrier including a roller that engages the surface of the engagement structure.

18. The system of claim 12, further comprising:
    a patient-side manipulator that physically acts on the adapter to cause actuation of the actuated element; and
    the sterile barrier positioned between the patient-side manipulator and the instrument, wherein the sterile barrier comprises:
    a sheet; and
    the adaptor mounted in the sheet, wherein the patient-side manipulator is connected to the adaptor and the adaptor is connected to the exposed portion of the drive member.

19. The system of claim 18, wherein the adaptor comprises a fork that connects to an engagement structure on a proximal end of the drive member.

20. The system of claim 19, wherein the patient-side manipulator pulls on the adaptor to move the drive member.

21. The system of claim 19, wherein the patient-side manipulator pushes on the adaptor to move the drive member.

22. The system of claim 18, wherein the adaptor comprises a gear that engages a gear rack on a proximal end of the drive member.

23. The system of claim 18, wherein the adaptor comprises a roller configured to contact a surface of the engagement structure, wherein the patient-side manipulator rolls the roller on the surface to move the drive member.

* * * * *